United States Patent [19]

Doumaux, Jr.

[11] Patent Number: 4,827,037

[45] Date of Patent: May 2, 1989

[54] QUALITY OF CATALYTICALLY PREPARED POLYALKYLENE POLYAMINES

[75] Inventor: Arthur R. Doumaux, Jr., Charleston, W. Va.

[73] Assignee: Union Carbide Corporation, Danbury, Conn.

[21] Appl. No.: 720,155

[22] Filed: Apr. 4, 1985

[51] Int. Cl.$^4$ .............................................. C07C 85/06
[52] U.S. Cl. .......................................... 564/479; 564/2; 564/478; 564/480; 564/497; 564/498; 564/512; 502/208
[58] Field of Search ............... 564/478, 479, 480, 512, 564/498, 497, 2

[56] References Cited

U.S. PATENT DOCUMENTS

| | | | |
|---|---|---|---|
| 3,714,259 | 1/1973 | Lichtenwalter et al. | 564/512 |
| 3,723,529 | 3/1973 | Pitts et al. | 564/2 |
| 3,819,710 | 6/1974 | Jordan | 564/497 |
| 4,123,462 | 10/1978 | Best | 564/480 |
| 4,404,405 | 9/1983 | Winters | 564/479 |
| 4,463,193 | 7/1984 | Johnson et al. | 564/479 |

FOREIGN PATENT DOCUMENTS

| | | | |
|---|---|---|---|
| 0058462 | 9/1982 | European Pat. Off. | 564/498 |
| 0093434 | 11/1983 | European Pat. Off. | 564/512 |
| 0115138 | 8/1984 | European Pat. Off. | 564/479 |
| 48-52708 | 7/1973 | Japan . | |

*Primary Examiner*—Glennon H. Hollrah
*Assistant Examiner*—S. Treanor
*Attorney, Agent, or Firm*—Gerald L. Coon

[57] ABSTRACT

Process for the improvement of the quality of polyalkylene polyamines prepared by the reaction of (i) ammonia and/or an alkyleneamine compound having at least two amino groups and an alkanolamine compound having at least one amino group in the presence of a catalytically effective amount of a metal acid phosphate and at a temperature and pressure sufficient to form the polyalkylene polyamine. When the polyalkylene polyamines, being produced by the process, have a dark black color which is measured as a Gardner Color Standard Number of at least 15 on the Gardner Color Scale and/or have a burnt or scorched odor, the inclusion of a sufficient amount of hydrogen with the ammonia and/or alkyleneamine compound and the alkanolamine compound, so that the hydrogen is in contact with the ammonia and/or alkyleneamine and alkanolamine in the reaction zone, will abate the burnt or scorched odor of the polyalkylene polyamines being produced and will lower the Gardner Color Standard Number of the polyalkylene polyamines being produced to 10 or below on the Gardner Color Scale. The best results are obtained by introducing the hydrogen along with the reactants into the reactor. By always using the hydrogen addition, one can abate or eliminate the poor quality problem from arising by thereby avoiding the production of such black, malodoriferous polyalkylene polyamines.

55 Claims, No Drawings

QUALITY OF CATALYTICALLY PREPARED POLYALKYLENE POLYAMINES

BACKGROUND OF THE INVENTION

The invention relates to the improvement of the quality of polyalkylene polyamines prepared from an alkyleneamine compound and an alkanolamine compound.

Amination by ammonolysis relates to those reactions in which an amino compound is formed using ammonia or a primary or secondary amine as the amination agent.

Historically, ethylenediamine was prepared from ethylenedichloride using such type of reaction. The ethylenedichloride was treated in a pressure autoclave with aqueous ammonia at 100° to 180° C., with ethylenediamine and amine hydrogen chlorides resulting. A large excess of ammonia was used in order to favor the formation of the primary amine over the various secondary products; even then only a 40 percent yield of the desired product was obtained. The reaction was non-catalytic. In general, the product obtained after neutralization of the amine salts from the process, upon separation of the product from the sodium chloride and usual by-products using conventional separation techniques, such as, distillation, had a color similar to the color of pure ethylenediamine and only the normal slight ammoniacal odor of polyethylene amines prepared using ammonia. Pure ethylenediamine is a clear, colorless, liquid which has an ammonia odor.

The ethylene dichloride route has comparatively high capital investment requirements and comparatively high utility costs, plus a number of environmental problems associated with it. The environmental difficulties associated with the ethylene dichloride route include side reaction to vinyl chloride and disposal of sodium chloride contaminated with organics.

The art subsequently developed catalytic processes for producing polyalkylene polyamines from an alkyleneamine compound having at least two amino groups and an alkanolamine having at least one amino group. Some of the catalytic processes also had ammonia or a primary amine or a secondary amine present as a reactant.

U.S. Pat. No. 4,463,193 discloses a process for preparing predominantly noncyclic polyalkylene polyamines. Ammonia or a primary or secondary amine is contacted with an alkanolamine compound having an amino group and having a primary or secondary hydroxy group and an alkyleneamine compound having two amino groups in the presence of a catalytically effective amount of a Group IIIB metal acid phosphate. A temperature is used which is sufficient to effect a reaction among the ammonia or amine, the alkanolamine compound and the alkyleneamine compound under a pressure sufficient to maintain a substantial amount of the ammonia or amine in the reaction zone. The polyalkylene polyamines produced by U.S. Pat. No. 4,463,193 are often of poor quality, having a dominant burnt-scorched odor which is quite objectional and having a very dark black color. The black color has been measured as being a Gardner Color Standard Number of 20 to 40 on the Gardner Color Scale. Such poor quality polyalkylene polyamines are poorly accepted on a commercial basis by the art. The art wants and uses polyalkylene polyamines which are much ligher, almost white, in color and which do not have such malodors.

Polyalkylene polyamines produced from an alkyleneamine having at least two amino groups and an alkanolamine having at least one amino group in the presence of a phosphorus-containing catalyst, such as, a metal phosphate or a cation exchange resin containing active phosphortic sites sometimes are also of similar poor quality. The burnt-scorched odor and dark black color of such poor quality polyalkylene polyamines are commercially unacceptable by the art.

Catalytic processes for the preparation of polyalkylene polyamines from ethylene oxide and ammonia using a reductive amination catalyst, such as, nickel on a support, are generally not susceptible to the production of such poor quality polyalkylene polyamines.

The following are a number of patents which have hydrogen present in reactors using various reductive amination catalysts. Applicants do not make any express or implied representation that the following patents are pertinent to applicants' invention in a patentable sense.

U.S. Pat. No. 4,404,405 discloses a continuous process for the manufacture of polyethylene polyamines. A continuous homogeneous fluid stream under pressure which contains ammonia, monoethanolamine, diethanolamine and triethanolamine (as produced by the direct reaction of ethylene oxide and ammonia) is provided. The amination feed stream is supplied to the amination zone, which is maintained at a superatmospheric pressure but sufficiently below the pressure of the amination feed stream to assure flow thereof through the amination zone and to form an amination product from containing ethyleneamines therein. The preferred catalyst is a solid material comprising nickel and rhenium on a support. The amination feed stream can optionally contain water, hydrogen and/or ammonia. The hydrogen may be supplied to the reaction zone as a separate feed stream into the amination zone or as a component of the amination feed stream. The hydrogen serves the purpose of a promoter for the catalyst. When hydrogen is not provided in the reaction zone and the catalyst is a nickel-rhenium catalyst as described above, the catalyst life is greatly shortened and the rate of amine production is materially reduced. By providing hydrogen in the amination zone, the catalyst is continuously promoted to effectively cause the amination of the alkanolamines to produce the desired products. Patent '405 states that it is believed that hydrogen acts as a continuously supplied inert to keep available sites at the catalyst surface for the desired reaction between ammonia and the ethanolamines and to preclude the stabilization of the catalyst sites by alkyleneamines and/or ammonia. The amount of hydrogen that should be present in the amination feed stream should be from about one mole percent to about 30 mole percent based on the total moles in the amination feed stream.

U.S. Pat. No. 3,714,259 discloses preparing polyethylene polyamines by reacting an ethyleneamine and an ethanolamine in the presence of a hydrogenation catalyst and under hydrogen pressure of 200 to 5,000 p.s.i.g. The catalyst is composed of oxides or salts of nickel, copper, iron, palladium, platinum, cobalt, chromium, rhodium, molybdenum and titanium. Promoters such as bauxite, pumice and kieselguhr can be used in combination with the catalyst.

U.S. Pat. No. 4,123,462 discloses producing ethylenediamine by reacting monoethanolamine with ammonia in the presence of hydrogen and a supported nickel-rhenium catalyst. The amount of hydrogen present is not critical. The hydrogen is added in an amount sufficient to keep the catalyst in an active state.

U.S. Pat. No. 4,209,424 discloses a catalytic process in a heterogenous phase for producing ethylenediamine and piperazine from ethanolamine and ammonia. The ethanolamine-ammonia reaction in the presence of the amination catalyst is conducted at a temperature between 170° and 260° C. at a pressure between 50 and 300 bars absolute. The ethanolamine, ammonia, and hydrogen are introduced into the reactor in quantities such that the ammonia-ethanolamine molar ratio is between 5 and 40 and the hydrogen flow rate is between 5 and 200 ml per mole of ethanolamine. The amination catalyst has at least one active metal from the group of transition metals consisting of nickel, cobalt and copper, uniformly combined with a refractory microporous substance.

U.S. Pat. No. 4,153,581 discloses a method of producing amines by contacting at reactive conditions at least one alcohol, aldehyde or ketone, or a mixture thereof, with an aminating agent in the presence of a catalyst. The catalyst is composed of cobalt, copper and a third component selected from the group consisting of iron, zinc, zirconium and mixtures thereof. The aminating agent can be, for example, ethylenediamine, and the alcohol can be ethanolamine. The method generally employs hydrogen. The amount of hydrogen employed can vary according to convenience but a typical minimum hydrogen:alcohol mole ratio is at least about 0.1:1.

U.S. Pat. No. 4,111,840 discloses the catalytic amination of lower aliphatic alkane derivatives, such as, alkanols, alkanediols and alkanolamines, using a nickel-rhenium catalyst. Hydrogen can be used in the reactor, but the amount of hydrogen gas present is not critical. Usually, the addition of hydrogen is done in an amount sufficient to bring the reaction mixture to the desired reaction pressure.

U.S. Pat. No. 4,254,060 discloses the production of aliphatic amines by reacting an aliphatic alcohol or an aliphatic aldehyde, with ammonia or a primary or secondary amine, in the presence of a homogeneous colloidal catalyst prepared by reducing a mixture of components. The mixture includes an inner complex salt of copper or silver, a carboxylate of copper or silver, an inner complex salt or a carboxylate of an element of Group VIII of the Periodic Table of Elements, manganese or zinc, and a fatty acid or an alkali metal or alkaline earth metal carboxylate. Preferably, the reaction is carried out in the presence of a small amount of hydrogen because the amounts of by-products having a higher boiling point are reduced and the reaction time is reduced to some extent.

U.S. Pat. No. 4,322,530 discloses a process for alkylating a polyamine by contacting, in a liquid media, a polyamine, an olefinic compound, carbon monoxide, and a hydrogen source in the presence of a catalytic amount of a rhodium atom-containing compound at a temperature of from about 50° to 250° C. and at pressure of from 30 to 300 atmospheres. The source of hydrogen can be water. Hydrogen can be used with the water, but poorer yields are obtained.

U.S. Pat. No. 4,210,605 discloses preparing aliphatic amines by reacting an aliphatic alcohol or an aliphatic aldehyde with ammonia or a primary or secondary aliphatic amine, in the presence of a homogeneous colloidal catalyst prepared by reducing a copper or silver salt of a carboxylic acid. The reaction can proceed even in the absence of hydrogen. However, it is preferred that the reaction by carried out in the presence of a small amount of hydrogen, because formation of high-boiling-point substances is reduced and the reaction time can be shortened to some extent.

U.S. Pat. No. 3,766,184 discloses catalytically converting aliphatic alcohols and aminoalcohols, and mixtures of aliphatic alcohols and aminoalcohols to aliphatic and heterocyclic amines by reaction with ammonia. The reaction is carried out in the presence of hydrogen and in the presence of a catalyst composition consisting essentially of iron and nickel and/or cobalt. The reaction betweenw the ammonia and the alcohol is carried out with ammonia in the presence of hydrogen gas, in order to ensure a good yield of the desired aliphatic amine product. The hydrogen can reduce a catalyst initially present as the oxides to the elemental metals. Generally, the quantity of hydrogen gas required is relatively small, and corresponds to a proportion of from about 2 to about 30 percent. Higher proportions of hydrogen can be employed, but generally, however, without any noticable benefit.

U.S. Pat. No. 4,229,378 discloses producing tertiary amines by reacting aliphatic, cycloaliphatic or araliphatic alcohols, aldehydes or ketones with ammonia, primary or secondary amines in the presence of a catalyst which is a mixture of copper, tin and an alkali metal supported on a suitable carrier. The reaction is preferably conducted in the presence of hydrogen, using partial pressures of hydrogen of from about 10 p.s.i.g. to about 3000 p.s.i.g. The catalyst is a reduction catalyst; the hydrogen provides a reducing atmosphere.

U.S. Pat. No. 4,206,149 discloses producing amines by reacting alcohols, aldehydes or ketones with ammonia, primary or secondary amines in the presence of a catalyst which is a mixture of copper and rhenium. The reaction is also preferably conducted in the presence of hydrogen.

U.S. Pat. No. 2,349,461 discloses preparing lower aliphatic amines having at least two carbon atoms attached to the nitrogen atom, by reacting hydrogen with a mixture of a lower aliphatic nitrile and at least one lower aliphatic aldehyde. The reaction is carried out in the presence of a hydrogenating catalyst at a temperature within the range of 180° to 400° C. An excess of hydrogen can be used.

U.S. Pat. No. 4,014,933 discloses a process for the production of an amine by reacting an alkanol having one to eighteen carbon atoms, or a cycloalkanol having five to twelve carbon atoms, or an alkanolamine, with ammonia or a primary or secondary amine in the presence of hydrogen and a cobalt-nickel copper-containing aluminum oxide or silicon dioxide supported catalyst at a temperature of from 100° C. to 200° C. and at a pressure of 10 to 250 atmospheres. 5 to 100 liters of hydrogen can typically be used per mole of alcohol.

U.S. Pat. No. 4,409,399 discloses a process for producing aliphatic amines by reacting an aliphatic alcohol or an aliphatic aldehyde with an aminating agent, which is ammonia, a primary amine and a secondary amine, in the liquid phase in the presence of an unsupported catalyst. The catalyst contains copper oxide or copper hydroxide, nickel oxide or nickel hydroxide, and, optionally, an oxide or an hydroxide of a Group IIA metal. Before using the catalyst, it is activated by reducing with hydrogen, preferably while it is dispersed within the reactant alcohol or aldehyde. This can be done, for example, by passing hydrogen therethrough while maintaining a temperature of about 100° to about 200°

C. over a period of about 15 minutes to about one hour at atmospheric pressure. In a preferred embodiment, the liquid alcohol or liquid aldehyde is charged to a stirred reaction vessel along with the desired catalyst mixture, after which the reaction vessel is purged with an inert gas, such as nitrogen. Then as the reaction vessel is heated to reaction temperature, the catalyst is activated by bubbling hydrogen into and through the liquid phase. When the desired reaction temperature has been reached, for example, in the range of about 150° to about 300° C. and the catalyst has been activated, a gas stream containing hydrogen and the reactant amine is passed through the reaction mixture.

The following patents are also of interest.

European Pat. No. 0,069,322 shows producing dimethylaminoethylmorpholine from morpholine and dimethylethanolamine in the presence of water and hydrogen at a temperature in the range of about 285° to 420° C., a pressure in the range of about 0.1 to 1.5 atmospheres, a liquid hourly space velocity of 0.05 to 1.5 in the presence of a catalyst which is a pyrophosphate, a monohydrogen phosphate or a dihydrogen phosphate of strontium, copper, magnesium, calcium, barium, lanthanum, or a mixture thereof.

U.S. Pat. No. 3,297,701 discloses producing diazabicyclo-(2.2.2)-octane and C-substitute diazabicyclo-(2.2.2)-octanes by contacting a metal phosphate catalyst with a piperazine compound, such as, N-hydroxyethylpiperazine. Examples of the metal phosphate catalysts include an aluminum phosphate, boron phosphate, iron phosphate, calcium phosphate, lithium phosphate, zinc phosphate, nickel phosphate, chromium phosphate, copper phosphate and cobalt phosphate. U.S. Pat. No. 3,297,701 states that hydrogen may also be employed in the process, for example, as a purge or carrier gas. Example XVII of U.S. Pat. No. 3,297,701 provided a 5 weight percent higher yield of ethyltriethylenediamine when hydrogen was used (at a space velocity of 3,440 cc./hr./cc./catalyst) than when no hydrogen was used.

U.S. Pat. No. 3,120,525 discloses the reaction of ammonia and an ethyleneic polyamine, such as, aminoethylpiperazine. The catalyst typically is a silica-alumina catalyst or a tungsten oxide catalyst. U.S. Pat. No. 3,120,525 states that, if desired, hydrogen can be added to the reactor, but no reason if given for the addition and the quantity to be added is not mentioned.

BROAD DESCRIPTION OF THE INVENTION

The invention broadly involves processes for improving the quality of polyalkylene polyamines.

More specifically, the invention involves processes for the improvement of the quality of polyalkylene polyamines prepared by the reaction in a reaction zone of a reactive nitrogen-containing compound selected from the group consisting of ammonia, a primary amine and a secondary amine, and an alkanolamine compound having at least one amino group in the presence of a catalytically effective amount of a phosphorus-containing compound, such as, a metal phosphate, and at a temperature and pressure sufficient to form the polyalkylene polyamines. The problem arises when the polyalkylene polyamines being produced by the process have a dark black color which is measured as a Gardner Color Standard Number of at least 15 on the Gardner Color Scale and/or have a burnt or scorched odor. By including a sufficient amount of hydrogen with the reactive nitrogen-containing compound and the alkanolamine compound, so that the hydrogen contacts the reactive nitrogen-containing compound and alkanolamine in the reaction zone, one abates the burnt or scorched odor of the polyalkylene polyamines being produced and lowers the Gardner Color Standard Number of the polyalkylene polyamines being produced to 10 or below on the Gardner Color Scale. While the hydrogen can be introduced into the reactor while the reaction is under way, the best results are obtained by intermingling the hydrogen with one or more of the reactants being fed into the reactor.

The art has not appreciated the advantages of injecting hydrogen into a reaction zone wherein polyalkylene polyamines are produced using metal acid phosphates and other phosphorus-containing catalysts or treating such polyalkylene polyamines with hydrogen to eliminate the malodors and/or dark color of polyalkylene polyamines.

Addition of hydrogen to the reactor also allows the use of comparatively high reaction temperatures.

Instead of waiting to introduce hydrogen into the reactor until it is discovered that poor quality polyethylene polyamines are being produced, it is especially advantageous to always use the hydrogen addition. This prevents of the poor quality problem from arising by avoiding the production of such black, malodiferous polyalkylene polyamines.

The invention process is most effective and preferred for use with the production of polyalkylene polyamines by the reaction of (a) an alkanolamine having at least one amino group and (b) a reductive nitrogen-containing compound selected from the group consisting of ammonia, a primary amine and a secondary amine, and/or in the presence of a catalytically effective amount of a solid, insoluble, Group IIIB metal acid phosphate and at a temperature sufficient to form such polyalkylene polyamines. Such production process is particularly susceptible to the production of polyalkylene polyamines having a burnt-scorched odor and/or having a dark black color which is measured as a Gardner Color Standard Number of at least 15 on the Gardner Color Scale. The use of sufficient hydrogen in the reactor will allow production of polyalkylene polyamines which do not have the burnt-scorched odor and which have a Gardner Color Standard number of 10 or less on the Gardner Color Scale.

A further advantage of the use of Group IIIB metal acid phosphates as catalysts is that such avoids problems associated with co-production of stoichiometric quantities of an inorganic salt. Furthermore, in contrast to many Group IA acid phosphates, Group IIIB metal acid phosphates are insoluble in the reaction medium. Thus, under conditions for operation of the process, Group IIIB metal acid phosphates are insoluble solids that are easily localized in a fixed bed or continuous stirred tank reactor. Isolation of polyalkylene polyamine products, particularly in continuous processes, is therefore readily accomplished.

DETAILED DESCRIPTION OF THE INVENTION

As used herein, all parts, ratios, proportions and percentages are on a weight basis and all temperatures are in degrees Centigrade, unless otherwise stated herein or otherwise obvious herefrom to one ordinarily skilled in the art. Also as used herein, the term "ethanolamine" specifically means monoethanolamine unless otherwise indicated or implied herein. U.S. Sieve Series mesh sizes are used herein.

The invention involves polyalkylene polyamine production from (a) a reactive nitrogen-containing compound selected from the group consisting of ammonia, a primary amine and a secondary amine, and/or an alkyleneamine compound having at least two amino groups and an alkanolamine compound having at least one amino group, or (b) such alkyleneamine compound and such alkanolamine compound plus ammonia or a primary amine or a secondary amine. When such polyalkylene polyamine production methods used phosphorus-containing catalysts, particularly metal phosphate catalysts, the result can be a poor quality polyalkylene polyamine having a dark black color and/or an offensive burnt-scorched color. By the addition of a small amount of hydrogen to the reactor or the reactor feed, so that the hydrogen contacts the reactants in the reaction zone, the quality of the polyalkylene polyamines can be increased to commercially acceptable levels.

Sufficient hydrogen is used to prevent the polyalkylene polyamines being produced from having a burnt or scorched odor and to lower the Gardner Color Standard Number of the polyalkylene polyamine being produced to 10 or below on the Gardner Color Scale. Preferably about 1 to about 20 mole percent, based upon one mole of the alkanolamine compound, of hydrogen is used; and most preferably about 3 to about 8 mole percent, based upon one mole of the alkanolamine compound, of hydrogen is used. More broadly, 0.1 to 30 mole percent of hydrogen (even more can be used, but it is not economical) can be used per mole of the alkanolamine.

Good quality polyalkylene polyamines only have a very weak ammoniacal odor which is a characteristic of polyalkylene polyamines produced using ammonia (particularly by the ethylenedichloride process). The presence of alkylamines in the polyalkylene polyamine can give the latter a fishy odor. When polyalkylene polyamines are produced by phosphorus-containing catalysts, such as, metal phosphate catalysts, particularly Group IIIB metal acid phosphate catalysts, the polyalkylene polyamines may have an offensive burnt-scorched odor. The hydrogen addition of the invention prevents the production of poor quality polyalkylene polyamines having such an offensive burnt-scorched odor.

Commercially-acceptable or good quality polyalkylene polyamines have a color which is measured as a Gardner Color Standard Number of 10 or less on the Gardner Color Scale. Preferably the Gardner Color Standard Number is 5 or less. The Gardner Color Scale was developed by Gardner Laboratory of Bethesda, Maryland 20014. The Gardner Color Scale starts with a number of 1, which is white, and progresses with larger numbers progressive representing progressively darker colors (from white to dark black). (Shades of white below the number one are usually graded using the platinum cobalt scale.) Gardner Color Standard Number 45 is a very dark black. Gardner Color Standard Numbers 15 to 45 range from black to very dark black, respectively. A Gardner Color Standard Number of 5 is an off-white, whereas a Gardner Color Standard Number of 9 is a very light yellow-brown-black color. The lighter and whiter the color, the more commercially acceptable is the polyalkylene polyamine.

When polyalkylene polyamines are produced by phosphorus-containing catalysts, such as, metal phosphate catalysts, particularly Group IIIB metal acid phosphates, the polyalkylene polyamines may have an unacceptable black color, that is, a color measured as a Gardner Color Standard Number between about 15 and about 45 or higher on the Gardner Color Scale. The hydrogen addition of the invention prevents the production of such poor quality polyalkylene polyamines and allows the production of polyalkylene polyamines having a color measured as a Gardner Color Standard Number of 10 or less on the Gardner Color Scale.

Most preferably the hydrogen is mixed with the reactive nitrogen-containing compound and/or the alkyleneamine compound and/or the alkanolamine compound before the alkyleneamine and the alkanolamine compound enter the reactor. It is also advantageous to have the hydrogen mixed with the reactive nitrogen-containing compound and/or the alkyleneamine compound and/or the alkanolamine compound during substantially the entire duration of the reaction. The reaction is a continuous or batch reaction. Preferably the reaction is conducted in the vapor phase or supercritical phase, but the reaction can be conducted in the liquid phase. As sometimes used herein the phrase "gas phase" means vapor phase and supercritical phase.

By reaction zone is meant that vessel, e.g., autoclave, continuous stirred tank reactor or packed bed reactor, in which the catalyst is located and production of polyalkylene polyamines is effected.

In the reactor, the temperature for the reaction depends upon the particular starting materials, ratios of reactants, and most importantly, the activity of the catalyst bed. Preferably the process is conducted at a temperature between 125° to 425° C., preferably at a temperature between 220° and 350° C. and most preferably the temperature is between 260° and 300° C.

Preferably the reaction is conducted at a pressure greater than 100 p.s.i.g. and most preferably from 200 to 2000 p.s.i.g., although the pressure at the time of reaction should normally be within the range from about 50 to about 4,000 p.s.i.g. The reaction is best conducted at a temperature high enough to keep the reactants above their dew point. This may also mean at a pressure (first defined by temperature) which expresses the first quadrant using the critical point as the origin. Often the higher pressures can be obtained by the addition of the desired amount of ammonia to the reaction vessel.

Generally the reaction is conducted at a liquid hourly space velocity of reactants (e.g., EDA and MEA, or MEA, EDA and NH$_3$) is between 0.1 and 100 per hour, although the liquid hourly space velocity or reactants preferably is between 1 and 25 per hour.

Diluent gases can be utilized to help in the control of the reaction temperature and assist in maintaining the desired pressure. Normally, a gaseous diluent, such as, nitrogen, argon, water, helium and methane, can be used in the reactor to increase the pressure in a batch reactor and volumetric flow in a fixed bed reactor.

Although the reactions can be carried out in the batch mode, they are also amenable to continuous processes, for example, operation of a continuously stirred tank reactor or a packed bed reactor. The reaction is allowed to proceed until a desired conversion is obtained or the reaction is complete. Normally the reaction, when using a Group IIIB catalyst, is carried out within about 0.5 to 5 hours in the batch mode or residence times (based on alkanolamine and alkyleneamine components) of 0.1 to 4.0 hours in a continuous mode for practical levels of polyalkylene polyamine production.

The reactor can be an up-flow or down-flow reactor and can have a fluidized bed or most commonly, a fixed bed. The catalyst bed can contain inert particles which can be interspersed throughout the bed and/or form discrete layers, e.g., at an end or intermediary to the bed. The volume of the reaction zone containing such inert particles is the reaction zone volume for purposes of determining the feed rate. Preferably, the space velocity should not be so high that for the reactor geometry, a significant amount of backmixing occurs. Advantageously, the flow through the catalyst bed is substantially plug-type flow.

In place of hydrogen, hydrogen-producing compounds can be used.

The reaction which the invention deals with is the catalytic reaction of the alkanolamine having at least one amino group with the alkylene having at least two amino groups to produce polyalkylene polyamines. For example, the mole ratio of ethylenediamine to monoethanolamine can range from about 0.05:1 to 12:1, preferably is about 4:1 to 1:4, and most preferably is about 1:1.

The alkyelenamine having at least two amino groups is preferably an unbranched alkylene moiety, such as, ethylenediamine, and preferably has primary amino groups. The alkanolamine preferably has a primary or secondary hydroxyl moiety and preferably a primary amino group(s); and preferably, the alkanolamine has an unbranched alkylene moiety.

The alkanolamine compounds used in the invention process include those represented by the formula:

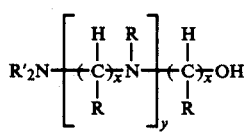

wherein R is hydrogen or a lower alkyl ($C_1$ to $C_4$) radical, R' is hydrogen or an alkyl ($C_1$ to $C_{25}$) radical, x is a number from 2 to 6, and y is a number from 0 to 3. Examples of suitable alkyl radicals are the lower ($C_1$ to to $C_4$) alkyls, such as, methyl, ethyl and butyl, and higher alkyls, such as, octyl, decyl and octadecyl. Methyl is the preferred lower alkyl radical. However, it is preferred that R and R' both are hydrogen; thus the alkanolamine would contain a primary amino group. Examples of such alkanolamine compounds are the ethanolamines, isomeric propanolamines, N-(2-aminoethyl)ethanolamine, N-methylethanolamine, N,N-dimethylethanolamine, N,N,N'-trimethylaminoethylethanolamine and the like.

The alkyleneamine reactants used in the invention process are represented by the formula:

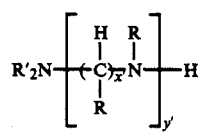

wherein R is hydrogen or a lower alkyl ($C_1$ to $C_4$) radical, R' is hydrogen or an alkyl ($C_1$ to $C_{25}$) radical, x' is a number from 2 to 6, and y' is a number from 1 to 4. Examples of suitable alkyl radicals are the lower ($C_1$ to $C_4$) alkyls, such as, methyl, ethyl and butyl, and higher alkyls, such as, octyl, decyl and octadecyl. It is preferred that R and R' are both hydrogen. The preferred lower alkyl radical is methyl. Examples of useful alkyleneamine compounds are 1,3-propylenediamine,N-methylpropylenediamine, 1,2-propylenediamine, diethylenetriamine, tributylenetetraamine, triethylethylenetetraamine, N,N,N'-trimethyldiethylenetriamine, noncyclic isomers of triethylenetetramine, noncyclic isomers of tetraethylenepentamine, N-methylethylenediamine, N,N-dimethylethylenediamine and ethylenediamine, which is the preferred alkyleneamine compound.

Ammonia and the preferred primary and secondary amines which are used in the invention process are represented by the formula:

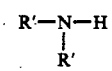

wherein R' is hydrogen or an alkyl ($C_1$ to $C_{25}$) radical, preferably a lower alkyl ($C_1$ to $C_4$) radical, such as, methyl or ethyl. Each R' can be the same as or different than the other R'. Useful amine feedstocks include monomethylamine, dimethylamine, monoethylamine, diethylamine, octylamine and octadecylamine.

Noncyclic polyalkylene polyamines that are produced by the reaction of (a) an alkyleneamine and an alkanolamine or (b) ammonia, an alkyleneamine and an alkanolamine or (c) ammonia and an alkanolamine are represented by the formula:

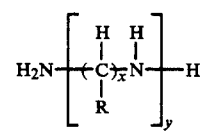

wherein R is hydrogen or a lower alkyl ($C_1$ to $C_4$) radical, preferably a methyl radical, X is a number from 2 to 6, Y is a number from 2 to 7, and X can vary for a given value of Y. Examples of such noncyclic polyalkylene polyamines that are produced are dipropylenetriamine, tributylenetetramine, di(2-methylethylene)triamine, tri(2-methylethylene)tetramine, N-(2-aminoethyl)-1,3-propylenediamine, diethylenetriamine, the noncyclic isomers of triethylenetetramine and the noncyclic isomers of tetraethylenepentamine.

Noncyclic polyalkylene polyamines include straight-chain and branched alkylene groups in such polyalkylene polyamines.

Cyclic polyalkylene polyamines that are produced by the reaction of (a) an alkyleneamine and an alkanolamine or (b) ammonia, an alkyleneamine and an alkanolamine or (c) an alkanolamine and ammonia are represented, for example by the following formula:

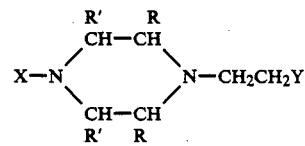

wherein R is hydrogen, an alkyl group containing 1 to 12 carbon atoms or a cycloalkyl group containing 6 to 12 carbon atoms, R' is hydrogen or an alkyl group containing 1 to 4 carbon atoms, X is hydrogen or —CH$_2$CH$_2$Y and Y is —OH or —NH$_2$.

Examples of cyclic polyalkylene polyamines are pierazine, N-(2-hydroxyethyl)piperazine, N,N-di(hydroxyethyl)piperazine, N-(hydroxyethyl)-2-methylpiperazine, N,N,'-di(hydroxyethyl-2-methylpiperazine, N-(hydroxyethyl)-2-ethylpiperazine, N,N'-di(hydroxyethyl)-2-ethylpiperazine, N-(hydroxyethyl)-2-butylpiperazine, N,N-di(hydroxyethyl)-2-butylpiperazine, N-(hydroxyethyl)-2-dodecylpiperazine, N-(hydroxyethyl)-2-cyclohexylpiperazine, N-(hydroxyethyl)-2-hexylcyclohexylpiperazine, N,N'-(dihydroxyethyl)-2,5-dimethylpiperazine, N-(hydroxyethyl)-2,3,5,6-tetramethylpiperazine, N,N'-di(hydroxyethyl)-2,5-dimethylpiperazine, N-(hydroxyethyl)-2,5-diethylpiperazine, N-(hydroxyethyl)diethylenetriamine, N-(hydroxypropyl)diethylenetriamine, N-(2-hydroxybutyl)dipropylenetriamine and morpholine.

The phrase "predominantly noncyclic polyalkylene polyamines" is meant to mean that such polyalkylene polyamines are mostly of the noncyclic species.

Use of secondary amines instead of ammonia leads to polyalkylene polyamines containing terminal dialkylamino groups. Alternatively, use of primary amines instead of ammonia leads to polyalkylene polyamines which contain randomly distributed monoalkylamino groups.

One embodiment of the invention comprises a continuous process for preparing good quality predominantly noncyclic polyalkylene polyamines by:

(a) adding a charge consisting essentially of ammonia or a primary or secondary amine and an alkanolamine compound to a reaction zone containing an alkyleneamine compound, hydrogen and a catalytically effective amount of a Group IIIB metal acid phosphate at a temperature sufficient to effect a reaction among the ammonia or amine, the alkanolamine compound and the alkyleneamine compound under a pressure sufficient to maintain a substantial amount of the ammonia or amine plus the hydrogen in the reaction zone to produce a reaction product stream containing ammonia or primary or secondary amine, alkanolamine compound, alkyleneamine compound, hydrogen and polyalkylene polyamines; and (b) withdrawing the product stream from the reaction zone and separating it to provide (i) a polyalkylene polyamine stream and (ii) ammonia or the primary or secondary amine, hydrogen, alkanolamine compound and alkylene compound, which are recycled to the reaction zone.

The invention can also be viewed as a method for substantially reducing the amount of alkyleneamine compound in the feed to the reaction zone in a continuous process for the preparation of good quality predominantly noncyclic polyalkylene polyamines comprises continuously adding a feed containing an alkanolamine compound, an alkyleneamine compound and hydrogen to a reaction zone containing a catalyst to yield a product stream comprising the polyalkylene polyamines, hydrogen, alkanolamine compound and alkyleneamine compound, separating the desired polyalkylene polyamines from the product stream and recycling the alkanolamine compound, alkyleneamine compound and hydrogen to the reaction zone. In the method: (a) (i) ammonia or a primary or secondary alkylamine and (ii) the hydrogen are added to the feed to the reaction zone; (b) a catalytically effective amount of a Group IIIB metal acid phosphate is used as the catalyst; and (c) the reaction is effected under a pressure sufficient to maintain a substantial amount of the ammonia or amine and hydrogen in the reaction zone.

To practice such a continuous process to make dialkylamino end-capped polyamines, the alkanolamine compound must be reacted with the dialkylamine in the presence of an N,N-dialkylalkylenediamine, i.e., an alkyleneamine compound with one primary amino group and one tertiary amino group. Similarly, when a monoalkylamine is substituted for ammonia, the alkyleneamine must have one primary amino group and one secondary amino group, e.g., N-methyl ethylenediamine would be used to make randomly mono-methyl substituted polyamines.

Other variations include the preparation of predominantly noncyclic polyamines derived from N-alkylalkanolamines. For example, the reaction of ammonia with N-methyl ethanolamine and N-methyl ethylenediamine also generates randomly methylated, although more highly methyl substituted, polyamines. However, if monomethylamine is substituted for ammonia, the polyamine becomes 100 percent methyl substituted, i.e., every nitrogen contains one methyl group. It should be apparent that in this and the former cases, the alkyleneamine whose concentration is to be maintained substantially constant is that which is formed by the reaction of the alkylamine or ammonia with the alkanolamine.

Any phosphorus-containing catalyst can be used. One group of preferred phosphorus-containing catalysts is the metal phosphate catalysts, which can be metal phosphates, metal monohydrogen phosphates, metal dihydrogen phosphates and metal pyrophosphates.

Lewis acid catalysts may also be useful and include Lewis acid salts of, e.g., sulfates, nitrates, halides as well as phosphates of Group IA, Group IIA, Group IIB, Group IIIA, Group IVB and the first row of Group VIII, and ammonium, e.g., lithium, sodium, potassium, cesium, aluminum, zinc, zirconium, antimony, tin(valence states II and IV), iron(valence states II and III), cobalt, magnesium, cadmium, etc. See, for instance, U.S. Pat. Nos. 4,316,840 and 4,399,308, herein incorporated by reference.

The catalysts used in the invention are heterogeneous catalysts. The catalysts are used in an amount of 0.1 to 12 weight percent, preferably 0.5 to 10 weight percent, and most preferably 2 to 7 weight percent, based on the total weight of the reactants.

The metal phosphate catalysts can be metal phosphates, metal monohydrogen phosphates, metal dihydrogen phosphates and metal pyrophosphates.

The metal phosphate catalysts include boron phosphate, aluminum phosphate, ferric phosphate, zinc phosphate, ferrous phosphate, nickel phosphate, chromium phosphate, copper phosphate and cobalt phosphate. Other metal phosphate catalysts which can be used are the phosphates of lithium, sodium, potassium, other metals of Group IA of the periodic table, beryllium, magnesium, calcium, other metals of Group IIA of the periodic table, titanium, zirconium, other metals of Group IV B of the periodic table, antimony and tin (valence states II and IV). Further useful catalysts are those which comprise a phosphorus bonded to a Group IV B transition metal oxide support, such as is disclosed in published European Patent Application No. 0115138 (the pertinent parts of which are incorporated herein by reference). Mixtures of two or more of the metal phosphate catalysts can be used.

The metal phosphate catalysts also include the pyrophosphates, monohydrogen phosphates and dihydrogen phosphates of strontium, copper, magnesium, calcium, barium, zinc, aluminum, cobalt, nickel, cerium, neodymium, and mixtures thereof. Specific examples of such catalysts are $SrHPO_4$, $Sr/BaHPO_4$, $Sr(H_2PO_4)_2$, $Ca(H_2PO_4)_2$, $CaHPO_4$, $Nd_2(HPO_4)_3$, $Ce_2(HPO_4)_3$, $CoHPO_4$, $NiHPO_4$, $Al_2(HPO_4)_3$, $MgHPO_4$, $BaHPO_4$, $CuHPO_4$ and $ZnHPO_4$.

The metal phosphate catalysts include the crystalline zirconium phosphate of U.S. Pat. No. 3,416,884 and the granular zirconium phosphate of U.S. Pat. No. 4,025,608—the pertinent parts of such patents are incorporated herein by reference.

The metal catalysts which are most preferred for practicing the process of the invention are group IIIB metal acid phosphates including Group IIIB metal phosphates, Group IIIB monohydrogen phosphates, Group IIIB dihydrogen phosphates and mixtures thereof. U.S. Pat. No. 4,463,193 (the pertinent parts of such patent are incorporated herein by reference) discloses processes for preparing the Group IIIB metal acid phosphates. While the intent of the catalyst preparation is to specifically provide a particular Group IIIB monohydrogen phosphate or dihydrogen phosphate, mixtures of the Group IIIB metal phosphates of the above-mentioned types may be obtained owing to complicated dependence of the catalyst composition on preparation conditions. Nevertheless, although the Group IIIB metal acid phosphate catalysts of the invention comprise the metal phosphates, monohydrogen phosphates, dihydrogen phosphates or mixtures thereof, the monohydrogen and dihydrogen phosphates of the Group IIIB metals are the preferred catalysts when in relatively pure form individually or in combination.

A Group IIIB metal is meant to include scandium, yttrium, lanthanum and the rare earth lanthanide metals having atomic numbers 58 to 71, and the rare earth actinides having atomic numbers 89 to 92.

The most preferred catalyst for the production of noncyclic polyalkylene polyamines are the Group IIIB metal acid phosphates, preferably the monohydrogen phosphates and dihydrogen phosphates of scandium, lanthanum, cerium, samarium, europium, thulium, erbium, ytterbium, yttrium, lutetium, thorium, neodymium, prasedymium, dysprosium and gadolinium.

The Group IIIB metal acid phosphate catalysts can be used for the production of polyalkylene polyamines either singly or in combination.

It is preferred to use those compounds which are more catalytically active and provide for substantial conversion to the monocyclic polyalkylene polyamine products. Examples of the most preferred catalyst compounds include lanthanum monohydrogen phosphate, lanthanum dihydrogen phosphate, lanthanum phosphate, praseodymium monohydrogen phosphate, praseodymium dihydrogen phosphate, praseodymium phosphate, neodymium monohydrogen phosphate, neodymium dihydrogen phosphate, neodymium phosphate and mixtures thereof.

The quantity of the acid phosphate salts of the Group IIIB metals used in the reaction can vary widely depending upon the reactivity of the catalysts and the reactivity of the reactants present. A catalytically effective amount of material is used; in other words, an amount which causes a reaction involving ammonia or an amine, the alkyleneamine and the alkanolamine to yield noncyclic polyalkylene polyamine products at the temperature and pressure used. Usually though, the amount used to provide a catalytic effect ranges from about 0.1 to 25 mole percent based upon the total amount of alkyleneamine and alkanolamine feed present in the reaction mixture, and preferably is an amount of about 0.1 to 10 mole percent. Within these ranges though, the level of catalyst is empirical and is adjusted depending on the product slate desired.

The Group IIIB metal phosphate catalysts used in the process of the invention can be prepared by the precipitation of the desired metal acid phosphate salt, washing the salt to remove inorganic co-products and drying the salt. Optionally, dried catalysts can be further processed prior to use for polyalkylene polyamine manufacture. Such processing is well known to those skilled in the art and includes extrusion or pelletizing, or compound with an inert support such as alpha-alumina.

Methods of preparing Group IIIB metal monohydrogen phosphate or dihydrogen phosphate are disclosed in U.S. No. 4,324,917 (the pertinent parts of such patent are incorporated herein by reference). Phosphate-containing materials can be obtained which consist predominantly of the Group IIIB metal phosphate, the Group IIIB metal monohydrogen phosphate, the Group IIIB metal dihydrogen phosphate, or mixtures in varying proportions of the Group IIIB metal monohydrogen and dihydrogen phosphate, and/or mixtures in varying proportions of any of the above Group IIIB metal acid phosphates with the Group IIIB metal phosphate. Such variations in catalyst composition can result from dependence of the catalyst composition on preparation conditions, such as temperature, concentration of reagents, stoichiometry of reagents, rate and order of reagent addition, pH of preparation, duration of preparation, volume and pH of water wash, duration of catalyst washing, and duration and temperature of catalyst drying. In any event, the Group IIIB metal acid phosphates obtained according to the general preparations referred to above are catalytically active for the production of polyalkylene polyamines.

Published European Patent Application No. 0115138 (the pertinent parts of which are incorporated herein by reference) discloses methods for preparing the catalysts comprising a phosphorus bonded to a Group IV B metal oxide support. Any appropriate liquid or liquefiable phosphorus compound can be used as a source of the phosphorus. For convenience, phosphoric acid will normally be used. However, other phosphorus compounds such as phosphoryl chloride ($POCl_3$), phosphorus acid, polyphosphoric acid, phosphorus halides, such as phosphorus bromide, alkyl phosphates and alkyl phosphites such as trimethyl phosphate, triethyl phosphate, trimethyl phosphite, triethyl phosphite, etc. may be utilized. Also, a diaminohydrogen phosphate such as diammonium hydrogen phosphate, $(NH_4)_2HPO_4$, dimethyldiamino hydrogen phosphate, diethylamino hydrogen phosphate, etc. may be used. The catalyst compositions are prepared by depositing a phosphorus compound on a support comprising an oxide of a Group IVb transition metal oxide. The group IVb transition metal oxides include the oxides of titanium, zirconium, hafnium and thorium. Pellets of the group IVb metal oxide may be prepared by extrusion or by compaction in conventional pelleting apparatus using a pelleting aid such as graphite. The phosphorus compound can be on a powdered IVb metal oxide followed by pelleting and calcination. Preferably the catalyst composition is prepared by impregnating a preformed pellet. A suitable procedure to be used is to heat a liquid containing the liquid or liquefiable phosphorus compound at a temperature of about 100° to about 150° C. and to then add pellets in an amount about equal to the volume of the heated liquid. This treatment should be continued from about 0.5 to about 5 hours. At the end of that time, the resulting mixture of pellets and liquid is cooled, decanted to remove excess liquid followed by washing with an amount of water adequate to substantially completely remove unadsorbed liquid. Temperatures about 150° C. can be used, if desired, but there is no particular advantage in doing so. It will be understood that the phosphorus that is present on a thus-treated pellet is not present as elemental phosphorus, but rather as phosphorus that is chemically bound, probably as an oxide, to the group IVb metal oxide support. However, the exact nature of the bonding is not completely understood.

European Patent Application No. 0115138 discloses an amount of phosphorus that is bonded or otherwise adheres to the support is a function of heating and other conditions used in the treating step and is also a function of the chemical identity of the phosphorus compound that is used as a source of phosphorus. Under the treating conditions exemplified above, at least about 2.5 weight percent of phosphorus is caused to bond or otherwise permanently adhere to the pellets. There is an upper limit to the amount of phosphorus that bonds or otherwise permanently adheres to the support. This upper limit is, as indicated, a function of both the treating conditions and the chemical used as a source of the phosphorus. Normally, the maximum amount of phosphorus that can be caused to bond or otherwise permanently adhere to the pellets is within the range of about 5 to 10 weight percent. As a master of convenience, the normal practice is to use only one chemical as a phosphorus source (e.g., phosphoric acid). However, mixtures of two or more such reagents may be used, if desired. Calcining is not mandatory if the pellets are impregnated at least at about 100° C., but the pellets can be calcined, if desired. Calcining is conducted for 2 to 24 hours at a temperature of 100° C. but below the temperature at which thermal destruction of the phosphorus bonding occurs. This can be determined experimentally for a particular catalyst. Temperatures above 900° C. should be avoided. A suitable calcining temperature range is normally 200° to 800° C. and, more preferably 500° to 700° C. Other procedures can be used n adding phosphorus to the group IVb metal oxide.

The pertinent parts of copending, commonly-assigned U.S. Patent Application Ser. No. 576,807, filed on Feb. 7, 1984, are incorporated herein by reference. U.S. Ser. No. 576,807 discloses certain phosphorus acid or acid derivative compounds which are useful phosphorus-containing catalysts within the scope of the invention herein. The term phosphorus acid or acid derivative defines compounds having a P-X bond wherein P is a phosphorus atom bonded to a halogen, oxygen, sulfur or nitrogen atom and X is a radical capable of (1) hydrolyzing to produce the corresponding phosphorus acid structure, or (2) exchanging with a hydroxyl group from the hydroxy alkylene reactant to provide a phosphorus ester.

The phosphorus acid or acid derivative catalyst of U.S. Ser. No. 576,807 is believed to function by forming with the alkanolamine or alkylene glycol compound a phosphorus ester in situ. For this reason, it is believed that a requirement for a good phosphorus catalyst is that it contain as a substructure an atom bonded to phosphorus that can be replaced readily by the oxygen atom of a hydroxyl group of the difunctional hydroxy alkylene compound. Such a replaceable atom might be oxygen (as in the case of phosphorus or phosphoric acids or their esters), halogen, nitrogen (as in the case of amides of phosphorus or phosphoric acids) or another atom that can be transformed into a phosphorus ester by a similar process.

Phosphorus-containing compounds such as trialkyl and triaryl phosphines and phosphine oxices, which contain no such exchangeable substructure, do not function as catalysts as defined in U.S. Ser. No. 576,807. Very sterically hindered phosphorus compounds such as hexaethyl phosphoric triamide, while containing the requisite exchangeable substructure and functioning to some extent, are less preferred catalysts because they undergo the exchange process with the alkanolamine or alkylene glycol hydroxyl moieties only slowly. Phosphorus acids are defined by those structures wherein X in the P-X radical is a hydroxyl radical. Acid derivatives are defined by structures wherein X is a substitute functional group. Various acid derivatives include: salts when —X is —O⁻M⁺ wherein M⁺ is a mono or polyvalent cation; amides when —X is bonded to the phosphorus atom through a nitrogen atom; anhydrides when —X contains a second phosphorus atom bonded to the first phosphorus atom through an oxygen atom; esters when —X is —OR; and so on with regard to other functional groups defined by —X. The precise phosphorus acid or acid derivative structure is not critical so long as it fulfills the following two functional requirements: (1) that it provides for the relatively selective production of predominantly linearly extended polyalkylene polyamines and (2) that it enables increased conversion rates for polyalkylene polyamine production when water is removed during the reaction, possibly due to the water-inhibited formation of phosphorus intermediate compound during the reaction.

The phosphorus acids or acid derivative catalysts of U.S. Ser. No. 576,807 include those having the formula:

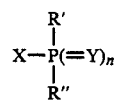

wherein Y is an oxygen or sulfur atom; n is 0 to 1; X is hydroxy, alkoxy, aryloxy, or the thio analogs of the foregoing, alkyl or aryl substituted amino, halo, or the salts or phosphorus anhydrides or thioanhydrides of the foregoing when X is hydroxy or mercapto; and R′ and R″ are hydrogen, alkyl, aryl or one of the groups previously defined by X.

Suitable phosphorus acid or acid derivatives of the U.S. Ser. No. 576,807 which can be employed include, for example, acidic metal or semi-metal phosphates, phosphoric acid compounds, and their anhydrides, phosphorus acid compounds and anhydrides, alkyl or aryl phosphates, alkyl or aryl phosphites, alkyl or aryl substituted phosphonic acids and phosphinic acids, alkali metal monosalts of phosphoric acid, phosphorus amides and phosphoric amides, the thioanalogs of the foregoing, and mixtures of any of the above. Suitable acidic metal or semi-metal phosphates include boron phosphate, ferric phosphate, aluminum phosphate and the like. Suitable phosphoric acid compounds include aqueous or anhydrous phosphoric acids, such as orthophosphoric acid, pyrophosphoric acid, metaphosphoric acid, and condensed phosphoric acids such as polyphosphoric acids. Any commercially available mono-, di-, or trialkyl or aryl phosphate or phosphate ester can be employed. In addition, bis(phosphates) and secondary phosphate esters, such as those disclosed in U.S. Pat. No. 3,869,526 and U.S. Pat. No. 3,869,527, respectively, can be utilized. Suitable alkyl or aryl substituted phosphonic acids or phosphinic acids include alkyl phosphonic acids, aryl phosphonic acids, alkyl phosphinic acids and aryl phosphinic acids. Examples of such phosphorus acid or acid derivative compounds include phenylphosphinic, ethylphosphonic, phenylphosphonic, naphthaphosphonic, and methylphosphinic acids; methyl phenylphosphonate, dimethyl phenylphosphonate, methyl phenylphosphinate, ethyl naphthalphosphinate, and propyl methylphosphonate; hexamethyl phosphoric triamide and their analogous phosphorus triamides. Preferred phosphorus catalysts include hexamethyl phosphorus triamide, hexaethyl phosphorus triamide, hexaethyl phosphorus triamide, boron phosphate, ferric phosphate, aluminum phosphate, phosphoric acid and phosphorus acid.

The amount of phosphorus acid or acid derivative catalyst of U.S. Ser. No. 576,807 utilized is a catalytically effective amount to cause condensation of the reactants to produce predominantly diethylenetriamine. This quantity will vary depending upon the reaction conditions and catalyst utilized. Usually a catalytically effective amount will be from about 0.01 to about 10 mole percent, and preferably from about 1 to about 3 mole percent, beased on the moles of hydroxy alkylene compound used.

The pertinent parts of copending, commonly-assigned U.S. Patent Application Ser. No. 606,000, filed on May 2, 1984, are incorporated herein by reference. U.S. Ser. No. 606,000 discloses certain phosphorus amide catalysts which are compounds having at least one phosphorus-nitrogen, i.e., P-N, bond. Preferably, the P-N bond is part of a P-N-H or P-N-C substructure. Compounds containing suitable P-N bonds can have three, four, or five substituents about the phosphorus.

Suitable compound catalysts of U.S. Ser. No. 606,000 having three substituents about phosphorus can be defined by the formula:

wherein Y is an unsubstituted or alkyl and/or aryl substituted amino radical; R' and R" are hydroxy, alkoxy, aryloxy, or their thioanalogs, hydrogen, alkyl, aryl, halo, or one of the groups previously defined by Y, and can be joined together with each other or with Y to form a phosphorus-containing heterocyclic ring. If R', R", and Y contains hydrogen bond to O, S, or N, such as when R' or R" is hydroxy or mercapto or Y is monoalkylamino, then corresponding metal salts containing P-O-M, P-S-M, or P-N-M linkages, where M is a monovalent or polyvalent metal or semimetal ion, and anhydrides, thioanhydrides, and condensed phosphorus amides containing respectively P-O-P, P-S-P, and P-N-P linkages can be suitable catalysts as well.

Suitable phosphorus amide catalysts of U.S. Ser. No. 606,000 having four substituents about phosphorus include those having the formula:

wherein X is an oxygen or sulfur atom, preferably oxygen, and Y, R', and R" are as defined above. As previously, corresponding metal and semi-metal salts and condensed phosphorus compounds may also be suitable.

Suitable phosphorus amide catalysts of U.S. Ser. No. 606,000 having five substituents about phosphorus include those having the formula:

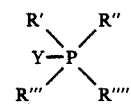

wherein Y is defined as above and R', R", R''', and R'''' are as defined for R' and R" above. As previously, corresponding metal and semi-metal salts and condensed phosphorus compounds may also be suitable.

Suitable phosphorus amide compouns which can be employed include, for example, the following compounds or their alkyl or aryl derivatives:
phosphoramidous acid, $H_2N—P(OH)_2$;
phosphordiamidous acid, $(H_2N)_2POH$;
phosphordiamidic acid, $(H_2N)_2P(O)(OH)$;
phosphoramidic acid, $H_2NP(O)(OH)_2$;
alkyl and aryl phosphonamidic acids, $RP(OH)NH_2$;
alkyl and aryl phosphonamidous acids, $RP(OH)NH_2$;
esters and half-esters of the foregoing, e.g. $H_2NP(OEt)_2$;
metal salts of the foregoing, e.g. $H_2NP(O)_2K_2$;
triaminophosphine, $(H_2N)_3P$;
triaminophosphine oxide $(H_2N)_3P(O)$;
alkyl and aryl phosphonic diamides, $RP(O)(NH_2)_2$;
alkyl and aryl phosphonous diamides, $RP(NH_2)_2$;
alkyl and aryl phosphinous amides, $R_2P(O)(NH_2)$;
analogs of the foregoing substituted with alkyl or aryl groups on nitrogen, e.g. $R_2NP(OH)_2$;
and thioanalogs of the foregoing, e.g. $R_2NP(S)(OEt)_2$.
The alkyl or aryl substituents on these substances can be linked to phosphorus through more than one atom, so as to form cyclic members of the above classes containing such heterocyclic rings as:

1,3,2-diazaphospholidine, 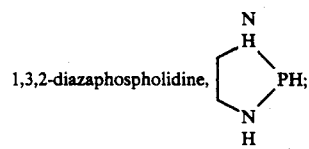

1,3,2-oxazaphospholidine, 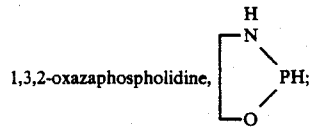

-continued tetrahydro-2H—1,3,2-oxazaphosphorine, 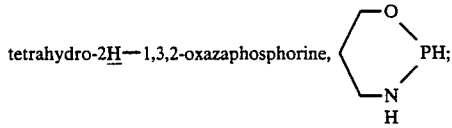

and the like. Such cyclic phosphorus amides can also be used as catalyst in the invention.

An additional class of phosphorus amides of U.S. Ser. No. 606,000 that can be be useful as catalysts in the invention comprises azaphosphoranes in which nitrogen is bound directly to phosphorus. Examples of such compounds include:

1,6-dioxa-4,9-diaza-5-phospha-(5-P$^V$)spiro [4.4]-nonane,

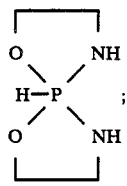

and 2,3,5,6,8,8-hexahydro-8-methyl- [1,3,2] oxazaphospholo [2,3-b] [1,3,2]oxazaphosphole,

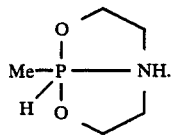

Preferred phosphorus amide catalysts of U.S. Ser. No. 606,000 include hexamethyl phosphorus triamide, hexaethyl phosphorus triamide and the phosphorus amide reaction product of ethylenediamine with phosphoric or phosphorus acid.

Phosphorus-containing cation exchange resins can be used in the invention and can be prepared by the methods disclosed in U.S. Pat. No. 4,324,917. The cation exchange resins provide exchangeable phosphorus-containing ions such as phoshonous, phosphonic, phosphoric, and phosphorous. Preferably the resins useful here are weak-acid cation exchange resins containing one or more of the above phosphorus-containing exchangeable ions. Duolite ® resins available from Diamond Shamrock Corp. are typical commercial phosphorous-containing resins. Examples of these are Duolite ES-62 ®, Duolite ES-63 ®, and Duolite ES-65 ® which are the phosphonous, phosphonic and phosphoric acid types, respectively.

Any of the non-resin catalysts useful in the invention can be supported on carriers, such as, silica, silica-alumina, silica-titania, alumina, diatomaceous earth (Kieselguhr) and any other conventionally-employed invert reactor packing material. Generally, the catalyst are supported. The active catalyst species are provided on the surface of the support through, for example, coating or impregnation. The catalyst (say metal) components on the support often comprise about 1 to 50, say, about 3 to 30, weight percent of the catalyst. Useful supports can be porous and have surface areas of from about 0.1 to 500, say, about 0.3 to 100, square meters per gram.

The catalyst can be of any convenient size or shape. Catalysts can be made in the form of powders, spherical or conical pellets, extruded strips and the like. Often, for commercial-scale operations, the pellets range in diameter from about 0.1 to 1 centimeter.

In the preparatin of noncyclic polyalkylene polyamines, and preferably the noncyclic polyethylene polyamines, using Group IIIB metal phosphate catalysts, the reaction is maintained at a temperature from about 125° to about 425° C., and most preferably is carried out between 260° and 300° C. to obtain a practical rate of polyalkylene polyamine production without generation of excessive levels of high molecular weight products.

The pressure utilized for carrying out the reaction, when using a Group IIIB metal phosphate catalyst, is that pressure which is sufficient to maintain a substantial amount of the ammonia or amine and hydrogen in the reaction zone and can, for example, range from 10 to 350 atmospheres in batch reactions, but preferably is that pressure which is sufficient to maintain the reaction substantially in vapor phase, at the temperature employed.

Although the reactions can be carried out in the batch mode, they are also amenable to continuous processes, for example, an operation of a continuously stirred task reactor or a packed bed reactor. The reaction is allowed to proceed until a desired conversion is obtained or the reaction is complete. Normally the reaction, when using a Group IIIB metal phosphate catalyst, is carried out within about 0.5 to 5 hours in the batch mode or residence times (based on the alkanolamine and alkyleneamine components) of 0.1 to 4.0 hours in a continuous mode for practical levels of polyalkylene polyamine production.

For continuous reactions, such as those carried out at controlled pressures in a fixed bed reactor or in a continuous stirred tank reactor, when using a Group IIIB metal phoshate catalyst, the pressure utilized for the reaction can range from 1 to 150 atm, but preferably is that pressure which is sufficient to maintain a substantial amount of the ammonia or amine in the reaction zone.

Failure to retain a substantial amount of the ammonia or amine in the reaction zone in either batch or continuous process will lead to high net consumption of alkyleneamine, owing to low production of the alkyleneamine by the amination of the alkanolamine. Reaction pressure must be sufficiently high, preferably at least 75 p.s.i.g., to maintain a significant portion of the ammonia or lower alkyl amine in the reaction zone. Preferred reaction times and catalyst levels depend on catalyst reactivity and are adjusted empirically. Thus, for example, relatively lower catalyst incorporations and shorter reaction times are preferred for the production of polyalkylene polyamines with more reactive catalysts.

Generally, the mole ratio of alkyleneamine compound to alkanolamine compound can range from about 0.05:1 to 12:1, and preferably is about 1:4 to 4:1.

With respect to the amount of ammonia or amine present in the reaction mixture (feed), the molar quantity of ammonia or amine can range from about 20:1 to 0.6:20 with respect to total alkyleneamine compound and alkanolamine compound, and preferably is about 12:1.25 to 1:1, although large excess quantities of ammonia or amine can be used. The ratios apply also to where the feed only contains ammonia (or amine) and the alkanolamine compound.

Recovery of the polyalkylene polyamines from the reaction mixture can be accomplished by conventional techniques, these techniques generally involving a distillation.

The starting reactants such as the lower alkanolamines can be produced in situ by the catalyzed reaction of ammonia with, for example the corresponding alkylene diol and/or epoxide. Likewise, the lower alkyleneamines can be produced from ammonia and the corresonding alkanolamine. Thus, in accordance with the invention, polyalkylene polyamines can be produced from the basic materials, for example, an alkylene oxide and ammonia, a small amount of hydrogen is present to assure that good quality polyalkylene polyamines are produced. It is preferred, however, that the desired alkanolamines and/or alkylenediamines be initially prepred, isolated and introduced into the instant process, along with the hydrogen, in desired quantities in accordance with the invention.

The invention process eliminates or avoids the abovementioned problems or disadvantages of the prior art. The invention process improves the quality of polyalkylene polyamines catalytically prepared from an alkylene compound and an alkanolamine compound. The invention process specifically prevents the formation of polyalkylene polyamines having a burnt-scorched odor and/or a dark black color. Also, the invention process provides polyalkylene polyamines which do not have a dark black color and which do not have a burnt-scorched odor.

Polyalkylene polyamines are useful as corrosion inhibitors, fabric softeners, lubricating oil additives, comonomes for polyamide resins, fungicides, surfactants, curing agents for epoxy resins and chelating agents.

Copending, commonly-assigned patent application entitled "Interreactor Separator", Ser. No. 720,151, concurrently filed with this application, is incorporated herein by reference. Such application discloses the use of a reductive amination reaction zone from which its effluent is separated into a, preferably, gaseous, MEA- and EDA-containing phase and a liquid, DETA-rich phase. The gas phase can be used for recycle (advantageously, it is at high pressure and suitable for recycle without undue energy penalties) or as a feed to another reactor which can use a reductive amination or other type (e.g., phosphorus-based catalyst) of catalyst.

Copending, commonly-assigned patent application entitled "Conversion Of Oxygen-Containing Polyamines", Ser. No. 720,154, concurrently filed with this application, is incorporated herein by reference. Such application discloses, in its broadest aspect, passing an oxygenated, polyethylenepolyamine feed in the presence of a nitrogen compound to a reaction zone containing a phosphorus-based catalyst. Advantageously, this feed is obtained from a polyethylenepolyamine reactor having a reductive amination catalyst. The feed typically contains AEEA.

Copending, commonly-assigned patent application entitled "Two Reactor Scheme Using Only Phosphorus-Containing Catalysts", Ser. No. 720,160, concurrently filed with this applicaton is hereby incorporated by reference. Such application discloses passing an oxygenated, polyethylenepolyamine feed in the presence of a nitrogen compound to a reaction zone containing a phoshorus-based catalyst. This feed is obtained from a polyethylenepolyamine reactor having a phosphorus-based catalyst. The feed typically contains AEEA.

Copending, commonly-assigned patent application entitled "Interchangeable Process Scheme", Ser No. 720,150, concurrently filed with this application, is incorporated herein by reference. Such application discloses processes for making and separating ethyleneamines, alkylamines, morpholines, etc., in the same process equipment. The separation systems required for these processes are very similar. Hence, block operation in the same reactor and separation equipment is achieved.

Copending, commonly-assigned patent application entitled "Preparation Of Diethylenetriamine With Azeotrope Recycle", (D-14876), concurrently filed withthis application, is incorporated herein by reference. Such application discloses processes for making ethyleneamines using a reductive amination or phosphorus-based catalyst in which a gaseous EDA/water phase is separated from the reactor effluent and at least a portion of the separated phase is returned to the reactor. In a preferred embodiment using a reductive amination catalyst, the recycle stream is admixed with MEA to break the azeotrope with water condensing out. Copending, commonly-assigned patent application entitled "Water Addition To Enhance Phosphoric Acid Salt Catalyst Activity", Ser. No. 720,159, concurrently filed with this application, is incorporated herein by reference. Such application discloses providing beneficial amounts of water in the reaction zone in which alkanolamine and another nitrogen compound are reacted to produce alkyleneamines over a phosphorus-based catalyst. The water is believed to enhance or maintain or regenerate catalytic activity.

Copending, commonly-assigned patent application entitled "Use of Pressure To Control The Noncyclics/-Cyclics Ratio Of Polyalkylene Polyamines", Ser. No. 720,158 concurrently filed with this application, is incorporated herein by reference. Such application discloses processes for producing polyalkylenepolyamines over phosphorus-based catalysts in which control of the ratio of noncylic to cyclic products is achieved by controlling the level of the reaction pressure.

The following compound abbreviations are sometimes used herein:
EDA—ethylenediamine
MEA—monoethanolamine
PIP—piperazine
AEP—aminoethylpiperazine
DETA—diethylenetriamine
TETA(NC)—triethylenetetramine (noncyclic isomers)
TETA(C)—triethylenetetramine (cyclic isomers)
TEPA(NC)—tetraethylenepentamine (noncyclic isomers)
TEPA(C)—tetrathylenepentamine (cyclic isomers)
HVY(NC)—pentaethylenehexamine and higher oligomeric polyethylene amines (noncyclic isomers)
HVY(C)—pentaethylenehexamine and higher oligomeric polyethylene amines (cyclic isomers)
AEEA—aminoethylethanolamine.

The following examples which illustrate the nature of the process are not intended to limit the scope of the invention. Unless otherwise noted, in each example the reactions were carried out under the indicated conditions either in a stirred 300 ml autoclave under that level of pressure and temperature which was sufficient to maintain a significant portion of the reaction in vapor phase. Such pressure ranged from 650 to 1600 p.s.i.g., depending on the feed ratio in the autoclave. In a fixed bed packed reactor, the back pressure regulator was set within the range of 200 to 1400 p.s.i.g.

Examples 1 to 3 are comparative, prior art examples.

EXAMPLE 1

A mixture of monoethanolamine (45.8 g, 0.75 mole), ethylenediamine (90.3 g, 1.50 mole), and lanthanum acid phosphate (10.2 g) is placed in a 300 ml stainless steel stirred autoclave. The mole ratio of ethylenediamine:monoethanolamine is 2:1 and the catalyst incorporation (level) is 7.49 weight percent based on the ethylenediamine and monoethanolamine. The mixture is heated to 300° C. for 2.0 hours during which time a pressure of 650 p.s.i.g. develops. During the reaction the mixture is stirred at 2000 rpm. Analysis of the cooled reaction mixtures by gas-liquid chromatography indicates substantial conversion of monoethanolamine and ethylenediamine to a mixture of predominantly noncyclic polyethylene polyamines [such as, EDA, MEA, TETA(NC) and AEEA]. The product mixture of polyethylene polyamines has a dark black color, that is, a color measured as a Gardner Color Standard Number of 44 on the Gardner Color Scale. The product mixture of polyethylene polyamines has a strong burnt-scorched odor which is very objectionable, offensive and dominant.

EXAMPLE 2

A mixture of monoethanolamine (24.9 g, 0.41 mole), ethylenediamine (48.3 g, 0.80 mole), ammonia (2 moles), and lanthanum acid phosphate (5.8 g) is placed in a 300 ml stainless steel stirred autoclave. The catalyst incorporation is 7.92 weight percent based on ethylenediamine and monoethanolamine. The mixture is heated to 300° C. for 2 hours during which time a pressure of 1600 p.s.i.g. develops. During the reaction the mixture is stirred at 2000 rpm. Analysis of the cooled reaction mixture by gas liquid chromatography indicates substantial conversion of monoethanolamine and ethylenediamine to predominantly noncyclic polyamines [such as, EDA, MEA, DETA, TETA(NC), TEPA(NC) and AEEA]. The mixture of polyethylene polyamines has a dark black color, that is, a color measured as a Gardner Color Standard Number of 44 on the Gardner Color Scale. The product mixture of polyethylene polyamines has a strong burnt-scorched odor which is very objectionable, offensive and dominant.

EXAMPLE 3

Lanthanum acid phosphate (10 cm$^3$ of −12 to −18 mesh particles) is charged to a fixed bed tubular reactor (18 cm$^3$ total volume) and overlaid with crushed vicor (5 cm$^3$ of −12 to −18 mesh particles). The reactor is heated to 265° C. in an insulated air oven. A mixture of ethylenediamine, monoethanolamine and ammonia (mole ratio of EDA:MEA:NH$_3$ is 1:1:6.9) is passed over the catalyst at a liquid hourly space velocity of 1.5 hr$^{-1}$, based on EDA and MEA, at 1400 p.s.i.g. Analysis of the cooled reaction product by gas/liquid chromatography indicates substantial production of predominantly noncyclic polyamines [such as, EDA, MEA, DETA, TETA(NC), TEPA(NC), and AEEA]. The mixture of polyethylene polyamines has a dark black color, that is, a color measured as a Gardner Color Scale. The product mixture of polyethylene polyamines has a strong burnt-scorched odor which is very objectionable, offensive and dominant.

Examples 4 to 6 are invention examples.

EXAMPLE 4

An admixture of monoethanolamine (45.8 g, 0.75 mole), ethylenediamine (90.3 g, 1.50 mole), hydrogen (sufficient amount to provide 5 mole percent per mole of the monoethanolamine), and lanthanum acid phosphate (10.2 g) is placed in a 300 ml stainless steel stirred autoclave. The hydrogen is metered in. The mole ratio of ethylenediamine:monoethanolamine is 2:1 and the catalyst incorporation (level) is 7.49 weight percent based on the ethylenediamine and monoethanolamine. The mixture is heated to 300° C. for 2.0 hours during which time a pressure of 650 p.s.i.g. develops. During the reaction the mixture is stirred at 2000 rpm. Analysis of the cooled reaction mixtures by gas-liquid chromatography indicates substantial conversion of monoethanolamine and ethylenediamine to a mixture of predominantly noncyclic polyethylene polyamines. The produced mixture of polyethylene polyamines has a very light yellow-brown-black color, that is, a color measured as a Gardner Color Standard Number of 9 on the Gardner Color Scale. The product mixture of polyethylene polyamines did not have a burnt-scorched odor and only has a very weak ammoniacal odor typical of high quality polyethylene amines.

EXAMPLE 5

A mixture of monoethanolamine (24.9 g, 0.41 mole), ethylenediamine (48.3 g, 0.80 mole), hydrogen (sufficient amount to provide 5 mole percent per mole of the monoethanolamine), ammonia (2 moles), and lanthanum acid phosphate (5.8 g) is placed in a 300 ml stainless steel stirred autoclave. The hydrogen is metered in. The catalyst incorporation is 7.92 weight percent based on ethylenediamine and monoethanolamine. The mixture is heated to 300° C. for 2 hours during which time a pressure of 1600 p.s.i.g. develops. During the reaction the mixture is stirred at 2000 rpm. Analysis of the cooled reaction mixture by gas liquid chromatography indicated substantial conversion of monoethanolamine and ethylenediamine to predominantly noncyclic polyamines. The product mixture of polyethylene polyamines has a very light yellow-brown-black color, that is, a color measured as a Gardner Color Standard Number of 9 on the Gardner Color Scale. The product mixture of polyethylene polyamines did not have a burnt-scorched odor and only has a very weak ammoniacal odor typical of high quality polyethylene polyamines.

EXAMPLE 6

Lanthanum acid phosphate (10 cm$^3$ of −12 to −18 mesh particles) is charged to a fixed bed tubular reactor (18 cm$^3$ total volume) and is overlaid with crushed vicro (5 cm$^3$ of −12 to −18 mesh particles). The reactor is heated to 265° C. in an insulated air oven. A mixture of ethylenediamine, monoethanolamine, hydrogen and ammonia (mole ratio of EDA:MEA:NH$_3$ is 1:1:6.9) is passed over the catalyst at a liquid hourly space velocity of 1.5 hr$^{-1}$, based on EDA and MEA, at 1400 p.s.i.g. The amount of the hydrogen in the mixture was sufficient to provide 5 mole percent per mole of the monoethanol. The hydrogen is metered in. Analysis of the cooled reaction product by gas/liquid chromatography indicates substantial production of predominantly noncyclic polyamines. The product mixture of polyethylene polyamines has a very light yellow-brown-black color, that is, a color measured as a Gardner Color Standard Number of 9 on the Gardner Color Scale. The product mixture of polyethylene polyamines did not have a burnt-scorched color and only has a very weak ammoniacal odor typical of high quality polyethylenepolyamines.

The invention products of Examples 4 to 6 are high quality polyethylene polyamines which are of a commercial degree readily acceptable by the art. This result is in contrast to the prior art products represented by Examples 1 to 3.

What is claimed is:

1. In a process for the production of polyalkylene polyamines in a reaction zone by the reaction of (i) a reactive nitrogen-containing compound selected from the group consisting of ammonia, a primary amine, a secondary amine, and alkylene amine compound having at least two amino groups, and (ii) an alkanolamine compound having at least one amino group in the presence of a catalytically effective amount of catalyst containing at least one of phosphorus and Lewis acid and at a temperature and pressure sufficient to form said polyalkylene polyamines, the improvement comprising, when said polyalkylenes polyamines being produced by said process have a color which is measured as a Gardner Color Standard Number of at least 15 on the Gardner Color Scale and/or have a burnt or scorched odor, contacting said nitrogen-containing compound and said alkanolamine compound with a sufficient amount of hydrogen in the reaction zone to abate the burnt or scorched odor of said polyalkylene polyamines being produced and to lower the Gardner Color Standard Number of said polyalkylene polyamines being produced to 10 or below on the Gardner Color Scale.

2. The process as claimed in claim 1 wherein said hydrogen is mixed with said reactive nitrogen-containing compound and/or said alkanolamine compound before said reactive nitrogen-containing compound and said alkanolamine compound enter said reaction zone, whereby said hydrogen is in contact with said reactants in said reaction zone.

3. The process as claimed in claim 2 wherein about 1 to about 20 mole percent, based upon one mole of said alkanolamine compound, of said hydrogen is used.

4. The process as claimed in claim 2 wherein about 3 to about 8 mole percent, based upon one mole of said alkanolamine compound, of said hydrogen is used.

5. The process as claimed in claim 2 wherein said hydrogen is contacted with said reactive nitrogen-containing compound and said alkanolamine compound in said reaction zone during substantially the entire duration of said reaction.

6. The process as claimed in claim 2 wherein said reaction is a continuous reaction.

7. The process as claimed in claim 2 wherein said polyalkylene polyamines in the absence of hydrogen have a color measured as a Gardner Color Standard Number between about 20 and about 45 on the Gardner Color Scale.

8. The process as claimed in claim 2 wherein said trreated polyalkylene polyamines have a color measured as a Gardner Color Standard Number between about 1 and about 5 on the Gardner Color Scale.

9. The process as claimed in claim 2 wherein said reaction is conducted in the vapor phase.

10. The process as claimed in claim 2 wherein said reaction is conducted in the supercritical phase.

11. The process as claimed in claim 2 wherein a gaseous diluent is added to said reaction step and wherein said reaction step is conducted in the vapor phase or supercritical phase.

12. The process as claimed in claim 2 wherein said reaction is conducted at a temperature between 220° and 350° C.

13. The process as claimed in claim 2 wherein said reaction is conducted at a temperature between 125° and 425° C. and at a pressure of at least one atmosphere.

14. The process as claimed in claim 2 wherein a gaseous diluent which is selected from the group consisting of helium, methane, nitrogen, argon, water or a mixture of at least two of such members, is added to said reaction zone.

15. The process as claimed in claim 2 wherein said reactive nitrogen-containing compound is ammonia and said alkanolamine compound is monoethanolamine.

16. The process as claimed in claim 2 wherein the mole ratio of said reactive nitrogen-containing compound to said alkanolamine compound is 20:1 to 0.6:20.

17. The process as claimed in claim 2 wherein said reaction is conducted at a temperature sufficient to keep said reactants and products above their dew points.

18. The process as claimed in claim 2 wherein said reaction is conducted at a pressure of about 50 to 4000 p.s.i.g.

19. The process as claimed in claim 2 wherein the liquid hourly space velocity of said reactants is between 0.1 and 100 per hour.

20. The process as claimed in claim 1 wherein said hydrogen is introduced into said reaction zone during said reaction.

21. The process as claimed in claim 20 wherein about 1 to about 20 mole percent, based upon one mole of said alkanolamine compound, of said hydrogen is used.

22. The process as claimed in claim 20 wherein about 3 to about 8 mole percent, based upon one mole of said alkanolamine compound, of said hydrogen is used.

23. The process as claimed in claim 20 wherein said hydrogen is introduced into said reaction zone during substantially the entire duration of said reaction.

24. The process as claimed in claim 1 wherein said polyalkylene polyamines in the absence of hydrogen have a color measured as a Gardner Color Standard Number between about 20 and about 45 on the Gardner Color Scale.

25. The process as claimed in claim 1 wherein said treated polyalkylene polyamines have a color measured as a Gardner Color Standard Number between about 1 and about 5 on the Gardner Color Scale.

26. The process as claimed in claim 1 wherein said phosphorus-containing catalyst in said reaction (a) is a phosphorus acid or a phosphorus acid derivative compound.

27. The process of claim 26 wherein the phosphorus acid or acid derivative compound has the structure:

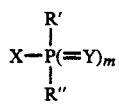

wherein Y is an oxygen or sulfur atom; m is 0 or 1; X is hydroxy, alkoxy, aryloxy, or the thioanalogs of the foregoing, alkyl or aryl substituted amino, halo, or the salts or phosphorus anhydrides or thioanhydrides of the foregoing when X is hydroxy or mercapto; and R' and R" are each hydrogen, alkyl, aryl or one of the groups previously defined by X, R' and R" can be the same or different.

28. The process of claim 26 wherein the phosphorus acid or acid derivative compound is phosphoric acid, phosphorus acid, boron phosphate, ferric phosphate, aluminum phosphate, hexaethylphosphorus triamide or hexamethylphosphorus triamide.

29. The process as claimed in claim 1 wherein said phosphorus-containing catalyst in said reaction (a) is a phosphorus amide catalyst which has at least one phosphorus-nitrogen bond.

30. The process as claimed in claim 29 wherein phosphorus amide catalyst has at least one P-N-C or P-N-H bond.

31. The process as claimed in claim 29 wherein the phosphorus amide catalyst is a phosphoramidous, phosphordiamidous, phosphoramidic, phosphordiamidic, phosphonamidous, or phosphonamidic acid, ester, half-ester, anhydride, or metal salt, a triamino phosphine or triaminophosphine oxide, a phosphonic or phosphonous diamide, a phosphinic amide, or a phosphonic amide.

32. The method as claimed in claim 29 wherein the phosphorus amide catalyst is a phosphorus or phosphoric alkyleneamide.

33. The process as claimed in claim 1 wherein said phosphorus-containing catalyst in said reaction (a) is a metal phosphate catalyst.

34. The process as claimed in claim 33 wherein said metal phosphate catalyst is a metal acid phosphate catalyst.

35. The process as claimed in claim 34 wherein said metal acid phosphate catalyst is a solid, insoluble, metal acid phosphate catalyst.

36. The process as claimed in claim 35 wherein said metal acid phosphate is a group IIIB metal acid phosphate, a Group IIA metal monohydrogen phosphate or a Group IIIB dihydrogen phosphate, and wherein said Group IIIB metal is scandium, yttrium, lanthanum or a rare earth lanthanide having an atomic number from 58 to 71.

37. The process as claimed in claim 36 wherein said phosphorus-containing catalyst is supported on a carrier.

38. The process as claimed in claim 34 wherein said metal acid phosphate catalyst is a Group II A metal acid phosphate catalyst or a Group IV B metal acid phosphate catalyst.

39. In a process for the production of polyalkylene polyamines in a reaction zone by the reaction of (a) an alkyleneamine compound having at least two amino groups, (b) an alkanolamine compound having at least one amino group and (c) a reactive nitrogen-containing compound selected from the group consisting of ammonia, a primary amine and a secondary amine, in the presence of a catalytically effective amount of a phosphorus-containing catalyst and at a temperature and pressure sufficient to form said polyalkylene polyamines, the improvement comprising, when said polyalkylene polyamines being produced by said process have a color measured as a Gardner Color Standard Number of at least 15 on the Gardner Color Scale and/or have a burnt or scorched odor, contacting said reactants (a), (b) and (c) with a sufficient amount of hydrogen in said reaction zone to abate the burnt or scorched odor of said polyalkylene polyamines being produced and to lower the Gardner Color Standard Number of said polyalkylene polyamines being produced to 10 or below on the Gardner Color Scale.

40. The process as claimed in claim 39 wherein said hydrogen is mixed with (a) said alkyleneamine compound and/or (b) said alkanolamine compound and/or (c) said reactive nitrogen-containing compound, before said reactants (a), (b) and (c) enter said reaction zone, whereby said hydrogen is in contact with said reactants (a), (b) and (c) in said reaction zone, and wherein said metal phosphate is a metal acid phosphate.

41. The process as claimed in claim 30 wherein about 1 to about 20 mole percent, based upon one mole of said alkanolamine, of hydrogen is used.

42. The process as claimed in claim 40 wherein about 3 to about 8 mole percent, based upon one mole of said alkanolamine, of said hydrogen is used.

43. The process as claimed in claim 40 wherein said hydrogen is contacted with said reactants in the reaction zone during substantially the entire duration of said reaction.

44. The process as claimed in claim 39 wherein said polyalkylene polyamines in the absence of hydrogen have a color measured as a Gardner Color Standard Number between about 20 and about 45 on the Gardner Color Scale.

45. The process as claimed in claim 39 wherein said treated polyalkylene polyamines have a color measured as a Gardner Color Standard Number between about 1 and about 5 on the Gardner Color Scale.

46. The process as claimed in claim 39 wherein said phosphorus-containing catalyst is a Group IIIB metal acid phosphate catalyst, a Group II A metal acid catalyst or a Group IV B metal acid catalyst.

47. In a process for the production of polyalkylene polyamines in a reaction zone by the reaction of (i) a reactive nitrogen-containing compound selected from the group consisting of ammonia, a primary amine and a secondary amine, and/or an alkyleneamine compound having at least two amino groups and an alkanolamine compound having at least one amino group in the presence of a catalytically effective amount of a phosphorus-containing catalyst and at a temperature and pressure sufficient to form said polyaklkylene polyamines, the improvement comprising, when said polyalkylene polyamines being produced by said process has a dark black color and/or has a burnt or scorched odor, contacting said alkyleneamine compound and said alkanolamine compound with a sufficient amount of hydrogen in said reaction zone to abate the burnt or scorched odor of said polyalkylene polyamines being produced and to provide said polyalkylene polyamines being produced with a color which is light brownish-black or lighter in the sense of a white color.

48. The process as claimed in claim 47 wherein said hydrogen is mixed with said alkyleneamine compound and/or said alkanolamine compound before said alkyleneamine and said alkanolamine compound enter said reaction zone, whereby said hydrogen contacts said reactive nitrogen-containing compound and/or said alkyleneamine and alkanolamine in said reaction zone.

49. The process as claimed in claim 48 wherein about 1 to about 20 mole percent, based upon one mole of said alkanolamine compound, of said hydrogen is used.

50. The process as claimed in claim 48 wherein about 3 to about 8 mole percent, based upon one mole of said alkanolamine compound, of said hydrogen is used.

51. The process as claimed in claim 47 wherein said polyalkylene polyamines in the absence of hydrogen have a color measured as a Gardner Color Standard Number between about 20 and about 45 on the Gardner Color Scale.

52. The process as claimed in claim 47 wherein said treated polyalkylene polyamines have a color measured as a Gardner Color Standard Number between about 1 and about 5 on the Gardner Color Scale.

53. The process as claimed in claim 47 wherein said metal phosphate is a metal acid phosphate.

54. The process as claimed in claim 53 wherein said hydrogen is introduced into said reaction zone during said reaction.

55. The process as claimed in claim 47 wherein phosphorus-containing catalyst is a Group IIIB metal acid phosphate, a Group II A metal acid catalyst or a Group IV B metal acid catalyst.

* * * * *